United States Patent
Kurtz et al.

(10) Patent No.: US 7,189,224 B2
(45) Date of Patent: Mar. 13, 2007

(54) SYSTEM AND METHOD FOR IMPROVED MATERIAL PROCESSING USING A LASER BEAM

(75) Inventors: Ronald M. Kurtz, Irvine, CA (US); Tibor Juhasz, Irvine, CA (US); Peter Goldstein, Santa Ana, CA (US); Imre Hegedus, Budapest (HU); Christopher Horvath, Irvine, CA (US); Gordon Scott Scholler, Poway, CA (US); Alan W. Berg, Rapid City, SD (US)

(73) Assignee: Intralase Corp., Irvine, CA (US)

( * ) Notice: Subject to any disclaimer, the term of this patent is extended or adjusted under 35 U.S.C. 154(b) by 160 days.

(21) Appl. No.: 11/083,793

(22) Filed: Mar. 18, 2005

(65) Prior Publication Data

US 2005/0165386 A1 Jul. 28, 2005

Related U.S. Application Data

(63) Continuation of application No. 10/394,368, filed on Mar. 21, 2003, now Pat. No. 6,902,561.

(60) Provisional application No. 60/367,119, filed on Mar. 23, 2002.

(51) Int. Cl.
*A61F 9/01* (2006.01)
(52) U.S. Cl. ............................... 606/5; 128/898; 606/4
(58) Field of Classification Search ............. 128/898; 606/4–5
See application file for complete search history.

(56) References Cited

U.S. PATENT DOCUMENTS

| | | | |
|---|---|---|---|
| 4,764,930 A | 8/1988 | Bille et al. | |
| 4,907,586 A | 3/1990 | Bille et al. | |
| 5,391,165 A * | 2/1995 | Fountain et al. | 606/4 |
| 5,549,632 A | 8/1996 | Lai | |
| 5,931,165 A | 8/1999 | Reich et al. | |
| 5,984,916 A | 11/1999 | Lai | |
| 5,993,438 A | 11/1999 | Juhasz et al. | |
| 6,090,100 A | 7/2000 | Hohla | |

(Continued)

FOREIGN PATENT DOCUMENTS

| | | |
|---|---|---|
| EP | 1 138 291 | 10/2001 |
| WO | WO 98/14244 A | 4/1998 |
| WO | WO 01/85044 | 11/2001 |

OTHER PUBLICATIONS

Ratkay-Traub I et al. Ultra-short pulse (Femtosecond) laser surgery. Initial use in LASIK flap creation. Ophthalmology Clinics of North American 2001; 14(2):347-55.

(Continued)

*Primary Examiner*—Henry M Johnson, III
(74) *Attorney, Agent, or Firm*—Connolly Bove Lodge & Hutz LLP (57) ABSTRACT

A method and system for improved material processing using a laser beam. The method and system includes directing a laser beam above, at or below the surface of the material in one or more preferred patterns and with preferred laser pulse characteristics specific to the material to reduce or mitigate the accumulation or effects of gas, debris, fluid, or other by-products of photodisruption either at the location where additional laser pulses are being placed or in other sensitive locations in the material.

24 Claims, 4 Drawing Sheets

U.S. PATENT DOCUMENTS

| | | |
|---|---|---|
| 6,099,522 A | 8/2000 | Knopp et al. |
| 6,110,166 A | 8/2000 | Juhasz et al. |
| 6,210,401 B1 | 4/2001 | Lai |
| 6,325,792 B1 | 12/2001 | Swinger et al. |
| 6,331,177 B1 | 12/2001 | Munnerlyn et al. |
| 6,344,040 B1 | 2/2002 | Juhasz et al. |
| 6,451,006 B1 | 9/2002 | Bille |
| 2002/0049450 A1 | 4/2002 | Myers |
| 2002/0087150 A1 | 7/2002 | Juhasz et al. |
| 2003/0014042 A1 | 1/2003 | Juhasz et al. |
| 2003/0073983 A1 | 4/2003 | Bille |
| 2004/0199149 A1 | 10/2004 | Myers et al. |

OTHER PUBLICATIONS

Ito M. et al. Picosecond laser in situ keratomileusis with a 1053-nm Nd:YLF laser. Journal of Refractive Surgery 1996; 12: 721-728.

Niemz MH et al. Intrastromal ablations for refractive corneal surgery using picosecond infrared laser pulses, Lasers and Light in Ophthalmology 1993; 5(3): 149-55.

Juhasz T. et al. corneal refractive surgery with femtosecond lasers. Journal of Selected Topics in Quantum Electronics 1999; 5(4): 902-910.

Niemz MH et al. Plasma-mediated ablation of corneal tissue at 1053 nm using a ND:YLF oscillator regenerative amplifier laser. Lasers in Surgery and Medicine 1991; 11:426-31.

Remmel RM et al. Intrastromal tissue removal using an infrared picosecond Nd:YLF ophthalmic laser operating at 1053 nm. Lasers and Light in Ophthalmology 1992; 4(3/4): 169-73.

Kautek et al, "Femtosecond-Pulse Laser Ablation of Human Corneas," Applied Physics A 58, pp. 513-518 (1994).

\* cited by examiner

SYSTEM AND METHOD FOR IMPROVED MATERIAL PROCESSING USING A LASER BEAM

RELATED APPLICATIONS

This application is a continuation of U.S. patent application Ser. No. 10/394,368, filed Mar. 21, 2003 U.S. Pat. No. 6,902,561 to U.S. provisional patent application 60/367,119, filed Mar. 23, 2002.

FIELD OF THE INVENTION

The present invention pertains generally to the field of material processing with a laser beam and more particularly to systems and methods for improved processing of these materials. The present invention is particularly useful for material processing utilizing laser photodisruption as a mechanism of action, particularly when such processing involves the use of multiple laser pulses placed on or below the surface of a material. While the field of the invention is very wide, it is particularly useful as a system and method for utilizing a laser beam to form a series of overlapping photodisrupted areas inside a material to define a new internal surface so that the anterior portion of the material can be moved to have access to the new internal surface of the material. A particular example of this application is in a type of ophthalmic surgery for correcting a patient's vision by removing at least a portion of an outer layer of the cornea. By creating a new internal surface within the bulk of the corneal tissue this procedure exposes underlying internal corneal tissue that can be altered to reshape the cornea and improve the patient's vision.

BACKGROUND OF THE INVENTION

There are three main classes of laser-material interaction: photocoagulation, photoablation, and photodisruption. Photocoagulation employs continuous wave laser light applied to absorbing material targets, with effects mediated by primary and secondary effects of thermal damage. This technique is most widely used in the eye to treat retinal diseases, such as diabetic retinopathy and macular degeneration. In photoablation, highly absorbing ultraviolet wavelengths are used to vaporize superficial materials, primarily for surface etching and refractive surgical applications in the cornea.

Photodisruption begins with laser induced optical breakdown (LIOB), when a laser pulse generates a high intensity electric field, leading to the formation of a mixture of free electrons and ions that constitutes the plasma state. The hot plasma expands displacing surrounding material. As the plasma expansion slows, the displacement front propagates through the material as a shock wave. The shock wave loses energy and velocity as it propagates, relaxing to an ordinary acoustic wave. The adiabatically expanding plasma quickly recombines and cools down, eventually forming a cavitation bubble. The constituents of the cavitation bubble depend on the make-up of the target material. For organic substrates, the cavitation bubble consists mainly of $CO_2$, $N_2$ and $H_2O$.

Using a photodisruptive laser and a delivery system, localized photodisruptions can be placed at or below the surface of a material to produce high-precision material processing. In one example of such material processing, internal surfaces can be created within the material by placing multiple pulses along a predetermined path. In special cases, these surfaces can be represented as planes placed in any orientation to create horizontal, vertical or oblique effects.

In using photodisruptive lasers, variable outcomes can result from the disposition of gas, debris, and other photodisruptive by-products. In some materials, photodisruption results, in formation of gas and water vapor. The behavior and effects of these and other by-products depend on the properties of the material surrounding them, as well as on the influence of additional laser pulses placed subsequently in the near vicinity. Generally, a gas bubble expands in size into the area of least resistance. With expansion, the gas cools and constituent gases, such as water vapor, can return to a liquid state. The presence of gas, liquid, debris and other by-products created during photodisruption in the region where additional laser pulses are being placed can be a cause of variable or undesired outcomes. The current invention represents an improvement over previous techniques utilizing laser photodisruption by offering elimination or mitigation strategies against these potential influences.

A specific application of the invention is in the use of a photodisruptive laser for the creation of a corneal layer in ophthalmic surgical procedures to correct vision errors. Vision impairment can occur for many reasons, and be the result of many causes. One common cause for vision impairment results from a defective condition of the eye which occurs when the refractive characteristics of the cornea do not cause parallel rays of light to focus on the retina. When the eye is at rest, and the rays of light focus in front of the retina, the condition is known as myopia (i.e. near-sightedness). On the other hand, when the rays of light focus behind the retina, the condition is known as hypermetropia or hyperopia (i.e. farsightedness). Both myopic and hyperopic conditions result in varying degrees of vision impairment. In most cases the conditions are correctable.

Eyeglasses or contact lenses are commonly used to correct myopic or hyperopic conditions. For various reasons, however, many persons who suffer with these conditions prefer not to wear eyeglasses or contact lenses. Alternative ways to correct these conditions include known surgical procedures for reshaping the cornea in various ways that are effective in changing its refractive characteristics. For example, in U.S. Pat. Nos. 4,665,913 and 4,669,466 to L'Esperance, a laser system is described which photoablates corneal tissue from the anterior surface of the eye. Another procedure is described in U.S. Pat. No. 4,988,348 to Bille, whereby corneal tissue is first removed to correct vision, and then the newly created surface is smoothed.

Rather than remove and reshape portions of the anterior portion of the eye to correct refractive defects, other procedures have been developed using a technique called intrastromal photodisruption for removing internal stromal tissue. Examples of such procedures and laser systems are described in U.S. Pat. No. 4,907,586 to Bille et al and U.S. Pat. No. 5,993,438 to Juhasz et al. Another example of a procedure for removing stromal tissue is the procedure described in U.S. Pat. No. 6,110,166 to Juhasz. In this procedure, an anterior corneal layer can be defined by using a laser to create a series of overlapping photodisrupted areas. The surgeon then separates the corneal layer by lifting it, to gain access to the underlying corneal tissue, the shape of which is changed with a photoablative laser, such as an excimer laser. The corneal layer is then repositioned on the cornea.

In prior practice, surgeons would create a corneal layer by focusing the laser beam at a starting point at or near the center of the to-be-formed corneal layer. The laser beam begins photodisrupting areas of tissue at the starting point, and is moved along a predetermined path, typically in a spiral pattern, from the center of the corneal layer to a predetermined circumference of the corneal layer. Finally, the laser beam is directed around the predetermined circumference to form a peripheral cut from the corneal layer to the outer surface of the cornea.

It has been observed in some cases that moving the laser beam along a predetermined path or pattern creates a temporary cloudy appearance, which is believed to result from gas and/or debris created during the photodisruption process that spreads inside the tissue because there are no outlets for the gas and debris. This condition is temporary; the gas and/or debris are eventually absorbed in surrounding tissue after a few minutes. Although this condition has no signficant side effects, spread of gas can influence the effectiveness of further laser pulses placed in the predetermined path in creating a high quality internal surface. Both the cloudy appearance and the less effective effects of ensuing laser pulses are considered undesirable.

It has also been observed that, in some cases and situations, moving the laser beam along a predetermined pattern creates fluid that can spread in the tissue and influence the effectiveness of further laser pulses placed in the predetermined path in creating a high quality internal surface. This fluid may result in surface irregularities that reduce the smoothness of the newly-created internal surface.

Thus, there is a perceived need for a predetermined path or pattern that does not cause gas and debris to spread in the tissue, or that does not lead to the above described creation or spread of fluid, both of which alter the character and effectiveness of further pulses placed along the predetermined path. As an alternative, even if these gas and/or fluid effects cannot be eliminated, the impact of these negative secondary effects also can be mitigated by choosing specific predetermined paths. Additionally, a need exists for a method and system to implement these desirable photodisruption patterns and predetermined paths.

A specific example of a desirable pattern or predetermined path involves reation of a secondary pattern or predetermined path connected or adjacent to the primary pattern or predetermined path. This reservoir can control the effects of by-products and/or gas from any type of pattern cut. Additionally, a need exists for a method and system to implement the reservoir. In conjunction with such a reservoir, or as an alternative approach, specific laser pulse placements and characteristics in the primary or secondary pattern or predetermined path can be chosen to control the effects of by-products and/or gas from any type of pattern cut.

SUMMARY OF THE INVENTION

In accordance with the present invention, a method and system have been developed for improved material processing using photodisruptive lasers. The method includes the steps of directing a laser beam at a starting point above, at or below the surface of a material and thereafter moving the laser beam from the starting point along a preferred predetermined path to reduce or mitigate effects of gas, debris and other by-products created during photodisruption in the region where additional laser pulses are being placed.

In one embodiment of the present invention, the preferred predetermined path has a starting point in a particular region of the material that reduces or mitigates effects of gas, debris and other by-products created during photodisruption in a more critical region of the material. As an example of this embodiment, the predetermined path may begin at the circumference of the pattern to be placed on or in the material to reduce or mitigate effects of gas, debris and other by-products created during photodisruption in the center of the pattern. Examples of this embodiment include moving the focal point along a predetermined path in a spiral pattern that starts at the predetermined circumference of the internal surfaces and runs toward the center of the predetermined circumference. In another embodiment, the predetermined path is in the shape of a raster pattern that runs back-and-forth through the material from a starting point near the predetermined circumference toward the opposite side of the predetermined circumference. In a third embodiment, the focal point of the laser beam is moved along a predetermined path in the shape of a series of concentric circles that runs from the starting point at or near the predetermined circumference toward the center of the predetermined circumference. While these embodiments localize the effects of gas, debris, and other by-products created at the start of photodisruption to the circumference of a pattern, the opposite effect can be chosen by choosing a starting point at the center of a pattern.

In another embodiment of the invention, material processing can be influenced through creation of a secondary pattern (with its own preferred pattern or predetermined path), that is connected or adjacent to the primary predetermined path. Gas, debris and other by-products created during photodisruption in the primary predetermined path can be significantly reduced or eliminated from the region of further laser pulse placement through creation of these so-called reservoirs.

In another embodiment of the invention, the effects of created secondary patterns can be optimized by choosing specific geometries and internal laser pulse characteristics, that may be different from those of the primary pattern. These include the area, depth, laser pulse to pulse distance (spot separation) and energy.

In another embodiment of the invention, material processing can be influenced by naturally occurring reservoirs in the material, if they allow the collection of gas, debris and other by-products created during photodisruption in the primary predetermined path. Secondary patterns or paths can be created to connect these naturally occurring reservoirs, with the effects on the primary pattern or path influenced by selection of specific geometries and internal laser pulse characteristics for these connecting patterns, which may be different from those of the primary pattern. These include the area, depth, laser pulse to pulse distance (spot separation) and energy.

In another embodiment of the invention, in the presence of an effectively operating reservoir, the specific laser pulse characteristics of the primary pattern or predetermined path can be chosen to reduce or mitigate effects of gas, debris and other by-products created during photodisruption in the area of further laser pulse placement. These include the area, depth, laser pulse to pulse distance (spot separation) and laser pulse energy.

When the material is the cornea of the eye and the goal is creation of a corneal layer, the predetermined path runs through the stromal tissue to define the corneal layer. An anterior internal surface can be formed with or without a hinge between the anterior internal surface and the peripheral cornea. The starting point of the primary predetermined path can be located either beneath the outer surface of the cornea or on the outer surface of the cornea. The predetermined path can be shaped such that the primary predetermined circumference is formed in a variety of shapes, for example generally circular or generally oval-shaped. The primary predetermined path can also be shaped such that the anterior internal surface is generally planar, generally convex, generally concave, or generally shaped to conform to the shape of any underlying excimer laser ablation in the tissue below the anterior internal surface.

Another aspect of the invention is directed to exposing an internal surface of the cornea with a predetermined circumference by forming a series of overlapping photodisrupted areas of stromal tissue to form a corneal layer, which has an anterior surface and a posterior surface. This corneal layer is at least partially removable from the cornea. The method includes the steps of positioning a focal point of a laser beam at a starting point in the vicinity of the predetermined circumference of the internal surface and photodisrupting tissue at the starting point, then moving the focal point of the laser beam from the starting point along a predetermined path and photodisrupting tissue along the path to create a pattern of overlapping areas across the internal surface to be exposed to form the corneal layer, and removing at least a portion of the corneal layer to expose the internal surface of the cornea. Additional embodiments of this aspect of the invention are similar to the ones described herein.

The method can also include the step of forming a peripheral surface that extends at an angle from the posterior internal surface to the outer surface of the cornea. The peripheral surface is formed by moving the focal point of the laser beam and photodisrupting tissue at a plurality of points along a path that runs from the vicinity of the anterior internal surface to the outer surface of the cornea. In one embodiment, the peripheral surface is formed at an angle of equal to or greater than 90 degrees relative to the posterior internal surface, while in another embodiment the peripheral surface is formed at an angle of less than 90 degrees relative to the posterior internal surface.

In the case of the creation of a corneal layer, gas in the interface where laser pulses are being placed can create interrupted areas of separation between the two surfaces. Liquid in the interface can create uneven surfaces. The former can occur when resistance is high in the horizontal location adjacent to the forming gas bubble, causing gas to spread in the cornea through spaces in the cornea, creating extraneous bubbles. If resistance is low in the horizontal location adjacent to the forming gas bubble, gas spreads horizontally and no extraneous bubbles are seen. The latter can occur if resistance is very low in the horizontal location adjacent to the forming gas bubble, then gas spreads very quickly, leading to rapid cooling and condensation of water vapor. This fluid can then seep back into the interface of the region where laser pulses are being placed. The presence of fluid in the interface of the region where laser pulses are being placed can result in a local depth change and the production of large feature surface abnormalities, such as ridges and waves.

In the case of creation of a corneal layer, a reservoir or secondary pattern or predetermined path can be optimized with the following parameters to reduce gas bubbles and improve corneal layer formation: larger reservoir area, greater depth, higher laser pulse:energy, and closer spot separation. To reduce the effects of fluid in the area where pulses are being placed, the opposite of the above scheme can be implemented.

In the case of creation of a corneal layer, the specific laser pulse characteristics of the primary pattern or predetermined path (i.e., the planar cut) can be optimized to reduce gas bubbles (and improve corneal layer formation): decrease spot separation and laser pulse energy. To reduce the effects of fluid in the area where pulses are being placed, the opposite of the above scheme can be implemented.

In the case of creation of a corneal layer, a reservoir and/or connection may be formed extending from the posterior internal surface to the periphery of the cornea towards or to the corneal-scleral junction (limbus). The reservoir may be at any angle to the posterior surface and can extend for any circumference or have any shape. This reservoir assists in the control of gas/liquid and debris accumulation. Additionally, the reservoir affects tissue separation/resection characteristics. Also, the reservoir affects character/quality of created surfaces for specific geometries and depth locations of the intended internal surface or surfaces that does not cause gas and debris to become trapped at the center portion of the removable layer. Although the reservoir herein is discussed in the context of corneal tissue the reservoir may be utilized in other tissue or non-biologic material to assist in the removal of debris where a primary photodisrupted cut is made.

The invention also includes a computer-readable medium having software embodied thereon to perform the steps described herein. In the case of an ophthalmic surgical system, a computer system is provided for directing a laser beam to create the desired patterns and laser pulse characteristics. The system includes an input control device for receiving the selection of a predetermined path from the user, a memory for storing a selection of predetermined paths, a processor unit coupled to the input control device and to the memory for processing the information inputted by the user to identify the selected predetermined path and performing the step of controlling the movement of the laser beam along the selected predetermined path, an output display for displaying the progress of the method, a laser source having the ability to focus and disrupt material above, at or below the corneal surface, and a focusing or directing mechanism for the laser source that is coupled to the processor unit and output display.

The invention also includes a femtosecond laser system that includes a laser source for generating a laser beam having the ability to focus and disrupt material above, at or below the surface and a processor for directing the laser beam to create a desired pattern. The system performs the steps of directing the focal point of the laser beam to a starting point, moving the focal point along a preferred predetermined path such that the effects of gas, debris and other by-products created during photodisruption are reduced or mitigated in the region where additional laser pulses are being placed. Another aspect of the invention is computer-implemented method for directing a laser beam to create a preferred predetermined path above, at or below the surface a material. A selection of a geometric border for a pattern cut is selected by a user or read from a file or database and received by the software where the selected geometric border parameter is stored into memory. The geometric border is displayed about an image of the material. A central point of the material may be determined for use in orienting the border about the material. The orientation is initially done programmatically; however, the user may reorient the geometric border. The type of pattern cut is selected by the user or read from a file or database and received by the software where the selected type of pattern cut is stored into memory. A laser beam is then directed to perform photodisruption of the material using the selected pattern cut for the selected geometric border. The photodisruption ordinarily occurs below the material surface based on a depth value. Among others, pattern types may be concentric, spiral, and rasterized. The photodisruption may create a horizontal resection of the material. The laser beam may then be directed to create a vertical resection of the about the circumference of the horizontal resection. A hinge may be created if the vertical resection is not made along the entire length of the circumference of the geometric border.

As intended for the present invention, the laser system to be used for accomplishing the methods will incorporate a beam of sequential laser pulses. Further it is contemplated that the duration of laser pulses in the beam will be in the nanosecond, picosecond or femtosecond ranges.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF THE PREFERRED EMBODIMENT

Figure 1:
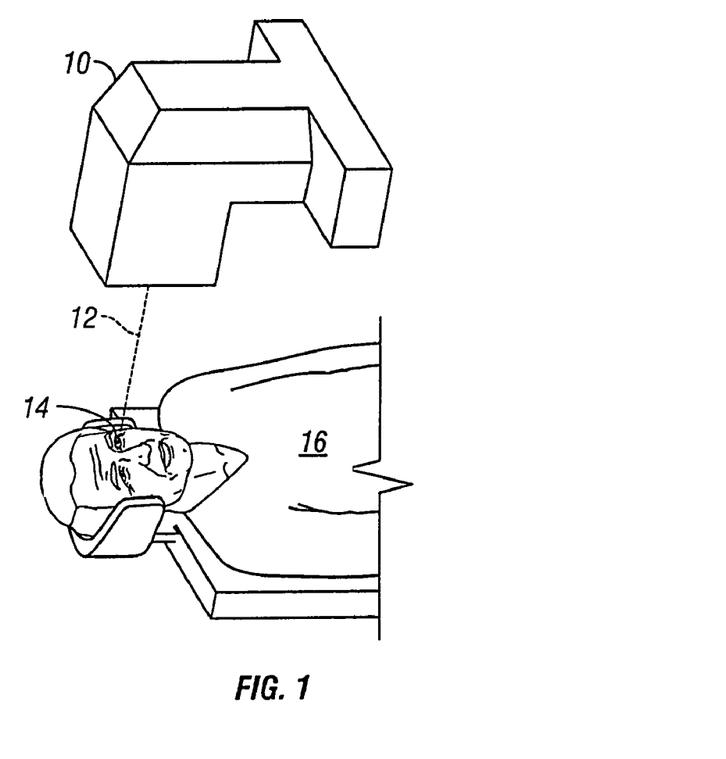
FIG. 1 is a perspective view of a patient being treated with the method of the present invention.

Referring initially to FIG. 1, an apparatus 10 for generating a laser beam 12 is shown. The laser beam 12 is directed onto an eye 14 of a patient 16. For purposes of the present invention, the apparatus 10 is capable of generating a pulsed laser beam 12 having physical characteristics similar to those of the laser beams generated by a laser system as disclosed and claimed in U.S. Pat. No. 4,764,930, which is exclusively licensed to the assignee of the present invention. Furthermore, the present invention contemplates the use of a pulsed laser beam 12 which has pulses with durations as long as a few nanoseconds or as short as only a few femtoseconds.

In one embodiment, a laser unit is controlled by software for photodisruption of the cornea utilizing a laser beam of constant energy, composed of an optical train of pulses with a duration of: approximately 600 femtoseconds at a repetition rate of up to several hundred thousand Hz. The actual energy in the emitted pulse train is determined by rotating a variable attenuator, an energy attenuation wheel, which operates under stepper motor control.

Energy measuring devices are placed in the optical path between the attenuator and safety shutters. These devices measure a constant fraction of the energy transmitted to the optical delivery system. The optical delivery system consists of an articulated arm, Z-axis lift, X-axis and Y-axis translation, X, Y, Z-axis galvanometer scanners, telescope, Z-axis focusing lens, turning mirror, microscope and a disposable applanation lens that makes the contact with the patient's eye.

The optical delivery system determines a 3-dimensional position in the patient's cornea at which the laser is focused. When the laser is pulsed, the energy delivered to the point of focus is sufficient to ionize tissue (photodisrupt) in a very small volume. Repetitively setting a focus point and pulsing the laser results in a resected plane of tissue.

Figure 2:
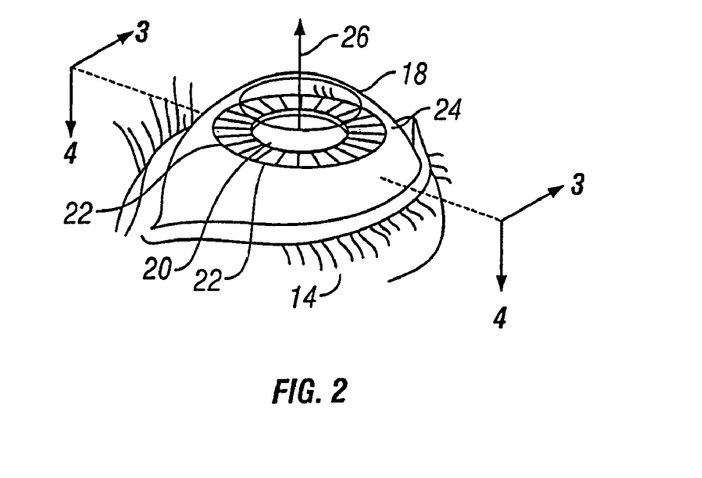
FIG. 2 is a perspective view of an eye.

FIG. 2 shows the anatomical structure of eye 14 and, specifically, that the cornea 18 is anterior to the pupil 20, the iris 22, and the sclera 24. Additionally, FIG. 2 indicates that the optical axis 26 of eye 14 passes through the cornea 18. Consequently, the tissue of cornea 18 is transparent to visible light.

Figure 3:
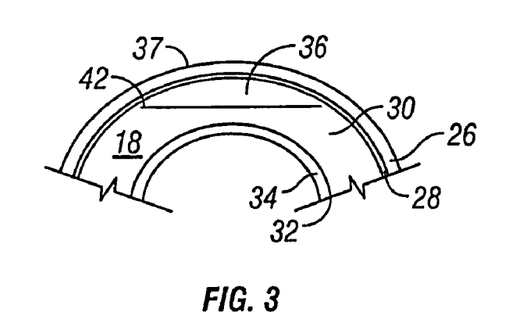
FIG. 3 is a cross-sectional view of the cornea of the eye as seen along the line 4—4 in FIG. 2 showing the creation of an anterior internal surface and a posterior internal surface, or alternatively, a corneal layer.

In FIG. 3 it can be seen that the cornea 18 includes five anatomically definable layers of tissue. Going in a direction from anterior to posterior in FIG. 3, the tissue layers of the cornea are: epithelium 26, Bowman's membrane 28, stroma 30, Decemet's membrane 32 and endothelium 34. The anterior internal surface 35 and posterior internal surface 38 are created by focusing the focal point of a laser beam at a predetermined starting point 42 and moving the focal point of the laser beam from the starting point 42 through the stromal tissue in a predetermined pattern to form a series of overlapping photodisrupted areas. Alternatively, a corneal layer 36 can be created in similar manner.

Figure 4:
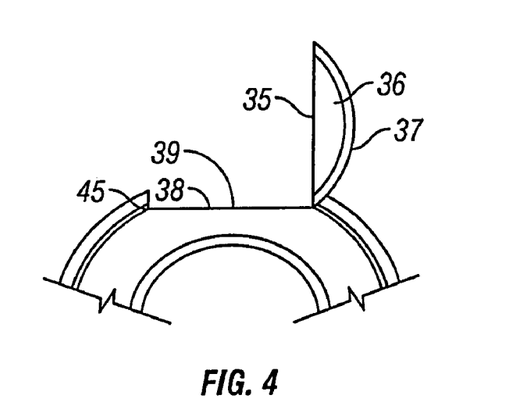
FIG. 4 is a cross-sectional view of the cornea of the eye as seen along the line 4—4 in FIG. 2 showing a removal of the anterior internal surface and exposing the posterior internal surface, or alternatively showing a removal of the corneal layer, exposing the internal surface of the cornea.

FIG. 4 shows the anterior internal surface 35 or the corneal layer 36 partially removed from the eye. The corneal layer 36 has an outer surface 37 that is the outer surface of the cornea. The corneal layer 36 may be completely removed from the eye, or may remain attached at a hinge, as shown in FIG. 4. The corneal layer 36 can be removed, as shown in FIG. 4, to expose the internal surface of the cornea 39 that is to be photoablated.

Figure 5:
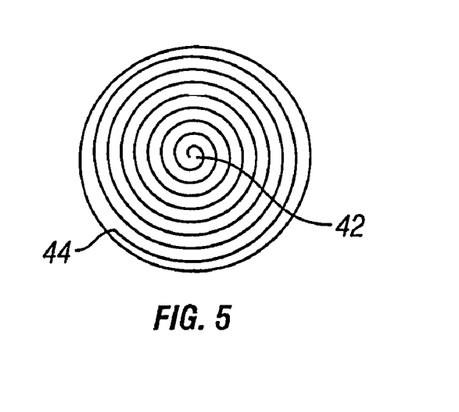
FIG. 5 is a plan view of the cornea of the eye as seen in the direction of the line 3—3 in FIG. 2 showing the path for movement of the laser beam in a outward spiral pattern to create the anterior internal surface and the posterior internal surface, or alternatively, the corneal layer.

The pattern of movement of the laser beam is one aspect of the present invention. Referring to FIG. 5, in prior practice, surgeons would choose a starting point 42 near the center of the corneal layer and move the laser beam in a pattern such as a spiral, working out to the predetermined circumference. As mentioned above however, it has been observed in some cases that this pattern can create a cloudy appearance in the center of the corneal layer. The cloudy appearance is the result of gas and debris that is created during the use of the laser. Due to the central-to-circumference spiral pattern, this gas and debris is trapped inside the cornea, as the outlets for the gas and debris are limited. This cloudy appearance is undesirable and may reduce the effectiveness of additional laser pulses being placed. Conversely, when created gas has access to a created or naturally occurring reservoir, fluid can reach the area where additional laser pulses are being placed, thereby interfering with the tissue separation and leading to an uneven surface.

Figure 6:
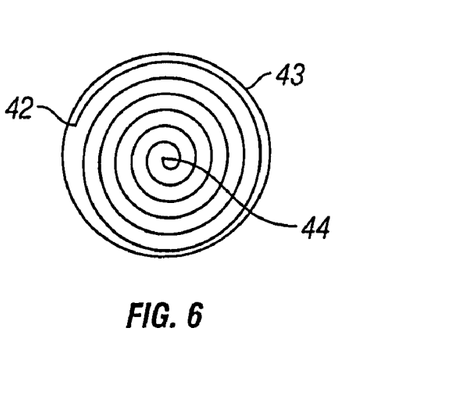
FIG. 6 is a plan view of the cornea of the eye as seen in the direction of the line 3—3 in FIG. 2 showing a path for movement of the laser beam in an inward spiral pattern to create the anterior internal surface and the posterior internal surface, or alternatively, the corneal layer.
Figure 7:
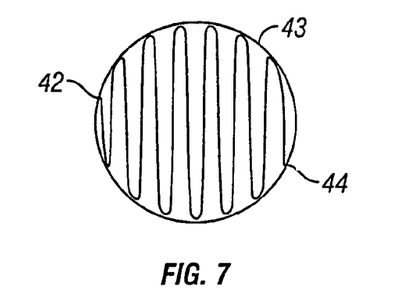
FIG. 7 is a plan view of the cornea of the eye as seen in the direction of the line 3—3 in FIG. 2 showing a path for movement of the laser beam in a raster pattern to create the anterior internal surface and the posterior internal surface, or alternatively, the corneal layer.

The present invention minimizes the accumulation of the gas, fluid, debris and other by products in the area where additional laser pulses are being placed or in other sensitive areas of the material undergoing processing. Referring to FIG. 6 for the case of the cornea, by selecting a starting point 42 below the surface of the cornea, substantially close to the predetermined circumference 43 of the corneal layer and moving the focal point of the laser beam along a pattern, such as the circumference-to-central spiral pattern shown in FIG. 6, or the raster pattern shown in FIG. 7, or the concentric-circle pattern shown in FIG. 8, to an ending point 44, the accumulation of gas and debris is minimized in the center, which reduces the cloudy appearance. The predetermined circumference 43 of the corneal layer 36 may be substantially in the shape of a circle or an oval. The figures illustrate various embodiments of creating a pattern. The illustrated figures are not meant to limit the patterns.

Figure 8:
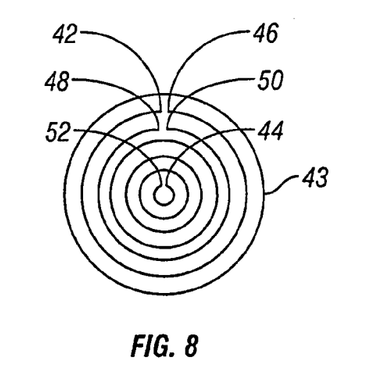
FIG. 8 is a plan view of the cornea of the eye as seen in the direction of the line 3—3 in FIG. 2 showing a path for movement of the laser beam in a concentric-circle pattern to create the anterior internal surface and the posterior internal surface, or alternatively, the corneal layer.

Note that in the concentric-circle pattern of FIG. 8, there will be a separate starting point for each concentric circle. The first starting point 42 is substantially close to the predetermined circumference 43 of the corneal layer. After the laser beam has been directed on a circular path, it will come to an ending point 46, substantially close to the first starting point 42. Then, the laser beam is directed to a second starting point 48 and is moved along a circular path to a second ending point 50, substantially close to the second starting point 48. This process is continued until the laser beam is directed to a final starting point 52 and is moved along a circular path to a final ending point 44, substantially close to the final starting point 52.

The predetermined path may be in a single plane, or may be a path such that the anterior internal surface 35 or internal surface of stromal tissue 39 is concave or convex.

Figure 9A:
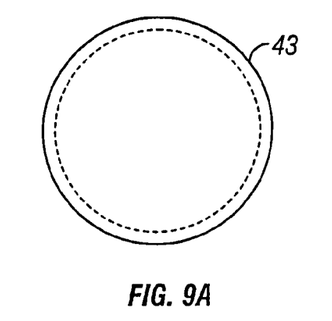
FIGS. 9a and 9b are plan views of the cornea of the eye as seen in the direction of the line 3—3 in FIG. 2 showing a path for movement of the laser beam to form the peripheral surface.
Figure 9B:
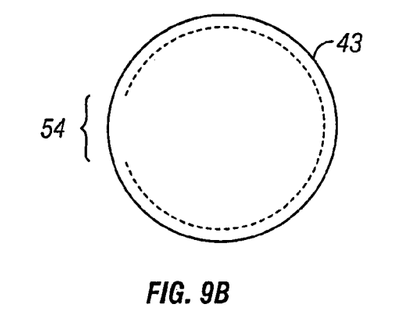

After the laser beam has been moved along the predetermined pattern, the laser is then directed to form a peripheral surface 45 around the predetermined circumference 43 of the corneal layer 36 or the anterior and posterior internal surfaces that connects the outer surface of the cornea 37 to the anterior internal surface 35 of the corneal layer 36. Forming the peripheral surface 45, shown by the dashed lines in FIGS. 9a and 9b, is accomplished by using the focal point of the laser beam to create a series of overlapping photodisrupted areas between the predetermined circumference of the corneal layer or anterior and posterior internal surfaces and the outer surface of the cornea, and can be performed such that the peripheral surface 45 is at an angle relative to the posterior internal surface 38. This angle can be greater than 90 degrees, such that the peripheral surface 45 and the posterior internal surface 38 form a bowl-shape, or it can be less than 90 degrees, such that the peripheral surface 45 and the posterior internal surface 38 form a conical-shape. To achieve an angle of greater than 90 degrees, the focal point of the laser beam is first directed around the predetermined circumference 43, and then is directed on a path of successively slightly larger circumferences, working toward the outer surface of the cornea. Conversely, to achieve an angle of less than 90 degrees, the focal point of the laser beam is first directed around the predetermined circumference 43, and then is directed on a path of successively slightly smaller circumferences working toward the outer surface of the cornea. To achieve an angle of exactly 90 degrees, the focal point of the laser beam is first directed around the predetermined circumference 43, and then is directed on a path of the exact same predetermined circumference, working toward the outer surface of the cornea.

The peripheral surface 45 may continue around the entire predetermined circumference 43, as shown in FIG. 9a, or may be discontinued before it has made a complete revolution around the predetermined circumference 43, leaving part of the corneal layer 36 or anterior internal surface 35 attached at a hinge 54, forming a flap, as shown in FIG. 9b. After forming the peripheral surface 45, the surgeon may remove the anterior internal surface 35 to expose the posterior internal surface 38 and finish the procedure. In the alternative aspect of the invention, the surgeon may remove the corneal layer 36 to expose the internal surface of stromal tissue 36 and finish the procedure.

To further reduce the accumulation of gas, fluid, debris and other by-products in the primary pattern or predetermined path, a secondary pattern or reservoir can be created peripheral or adjacent to the primary pattern to allow accumulation of gas and debris from the primary treatment pattern. This reservoir can be created prior to the creation of the main pattern in any shape and size, and preferably should connect to the main pattern either directly or through natural preexisting channels or potential channels in the cornea. Gas and debris can accumulate in this reservoir or drain peripherally through existing pathways of the eye.

Creating a fluid (gas) communication between the reservoir and the main pattern is preferred, but may not be necessary. Natural channels may serve the same purpose.

Providing a path or too easy a path for gas, fluid, debris and other by-products in the primary pattern or predetermined path may also have undesirable effects, because fluid can interfere in the region where laser pulses are being placed. In one embodiment, the optimal total area of the reservoir is about 10% that of the total area of the primary pattern cut. In another embodiment the pulse to pulse distance within the reservoir is greater than 6 microns and the pulse energy is less than 8 microjoules. In another embodiment, a small connection between the main pattern and the reservoir may be used, the size of which may further regulate effectiveness.

Increased drainage is a function of increased reservoir angle, increased reservoir diameter, and increased reservoir depth. Increased need for drainage is a function of increased area of the main pattern cut, shallower depth of main cut, and higher pulse energy in the main cut (which causes more gas to be produced). To increase control of drainage, the size of the reservoir is decreased, and the internal "resistance" of the reservoir is increased by decreasing the pulse energy and increasing the spot separation.

Figure 10A:
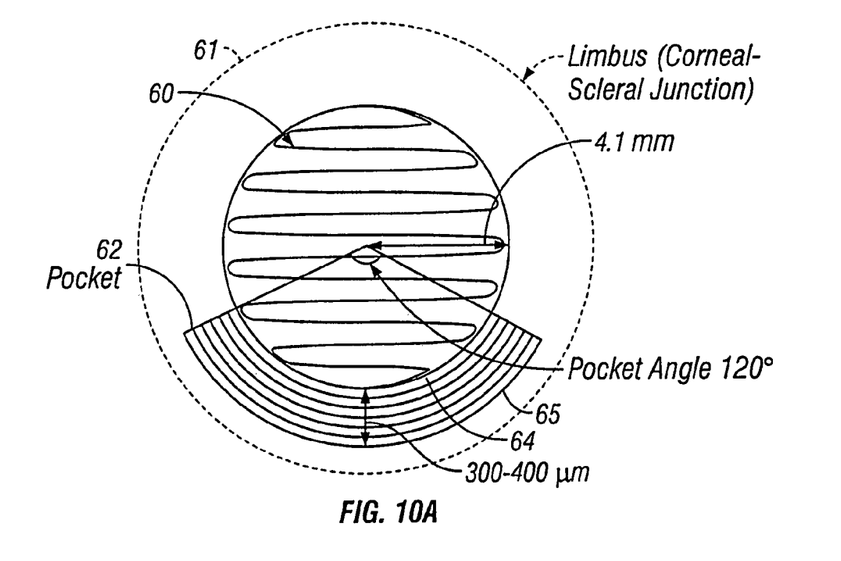
FIGS. 10a and 10b are plan views showing one embodiment of a reservoir formed adjacent to a pattern cut; and, FIG. 11 is a plan view showing another embodiment of a reservoir formed adjacent to a pattern cut.
Figure 10B:
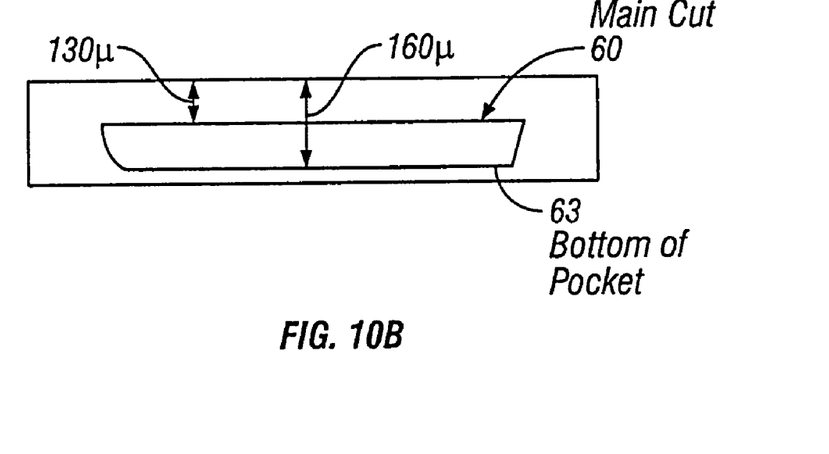

Referring to FIGS. 10a and 10b, one embodiment of a reservoir 62 is shown formed adjacent to a pattern cut 60. As exemplified, the primary pattern 60 is made as a raster pattern for the horizontal resection. However, other patterns may be used for the primary pattern. The particular placement, width, depth, and angle of the reservoir are made to accommodate the particular dimensions of the primary pattern. A reservoir 62 (also referred to as a pocket) is made adjacent to the main pattern cut 60, which in this example has a radius of 4.1 mm. The reservoir angle is 120° from about the central point of the eye. The width of the reservoir is about 300 to 400 µm from the first arc position 64 to the second arc position 65. The preferable pocket (reservoir)

angle is 45–90 degrees, and the preferable maximum pocket width is 300 microns. The reservoir 62 is preferably formed first, before making the main pattern cut. The bottom of the reservoir is shown at about 160 µm from the surface of the cornea. The second arc position is shown made adjacent to the limbus 61.

Figure 11:
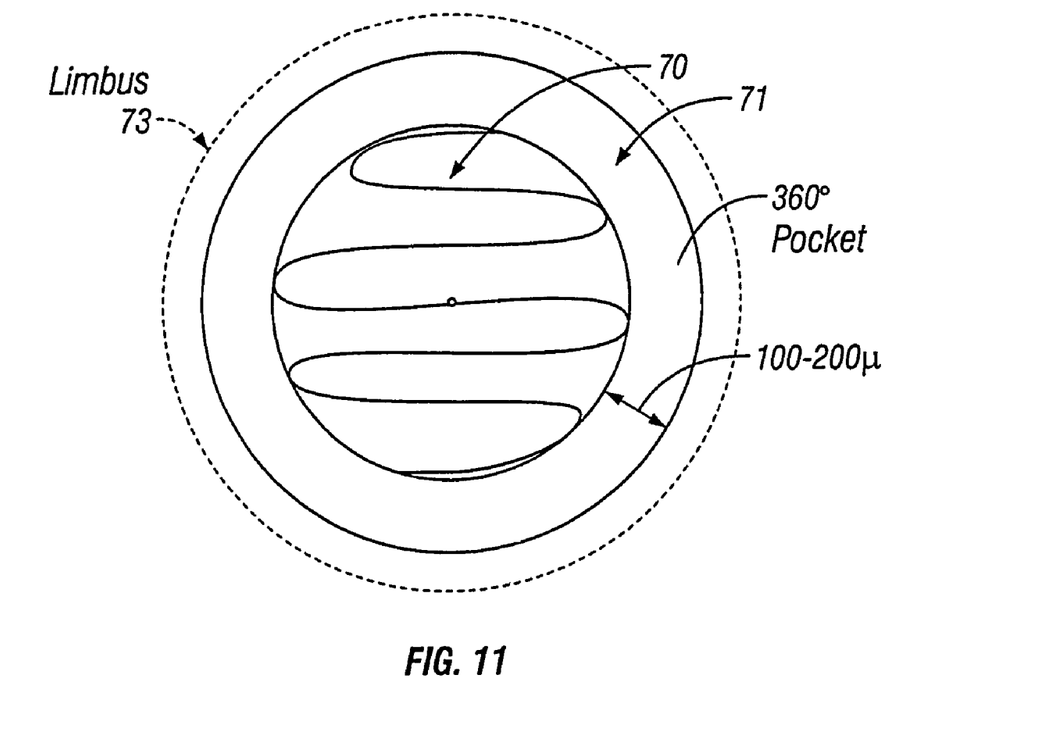

Referring now to FIG. 11, another embodiment of a reservoir 71 is formed adjacent to a pattern cut 70. In this embodiment, a complete 360° pocket circumscribing the horizontal resection 70 is created, but within the circumference of the limbus 73. In this example, the width of the reservoir is shown at about 100–200 µm. Preferably, the reservoir 71 should be made first, then the primary pattern 70 made.

One manner to implement the method of the present invention is to provide a laser unit with a computer system that directs a focal point of a laser beam to perform the method described herein. The computer system includes an input control device for receiving information from the user such as the selection of a predetermined pattern to be used in the method, memory for storing a selection of predetermined patterns, a processor unit coupled to the input control device and to the memory for processing the information inputted by the user to identify the selected predetermined pattern, an output display for displaying the progress of the method, a laser source having the ability to focus and disrupt tissue below the corneal surface, and a focussing mechanism for the laser source that is coupled to the processor unit and output display.

Another manner to implement the method of the present invention is to provide a software program that directs a focal point of a laser beam to perform the methods described herein. One embodiment of such a software program is a program operable with an input control device and an output display device. The input control device may be a keyboard, mouse, touch screen or other input devices used with computers. The output display device is a monitor or computer screen. The software program interacts with a database to store and retrieve data and parameters for the operation of the laser unit.

The software program, in addition to various other functionalities, provides for a selection or determination of a geometric border of the pattern cut, orientation of the geometric border over the cornea, direction of the laser beam movement, selection of type of pattern cut, and selection of additional patterns.

Determining geometric border of the pattern. The software program uses a defined geometric border for the circumference of the horizontal resection. The border sets the outside boundaries of the horizontal resection pattern. The software application may be configured to use only one geometric border, such as a circular border, as a standard default pattern. Alternatively, the software may be configured to allow the operator of the laser unit to select from a set of available geometric borders. Multiple pattern segments may be combined to create special or non-uniform geometric borders, for creation of reservoirs and drainage pathways. A user interface, typically a display monitor, presents the user with a selection of available geometric borders for horizontal resections of the corneal tissue. If the operator wants to select a different geometric border, the user selects a different border for the horizontal resection. For example, the software application may be configured to use a circle as a standard default geometric shape for horizontal resection. The laser unit operator, however, may select a different geometric border deciding that a different border, such as an oval, may be more advantageous for a particular patient.

Orienting the geometric border over the cornea. The geometric border is displayed over an image of the patient's eye. This image may be an actual image of the patient's eye, or a computer generated image of the eye. The geometric border is positioned such that the center of the geometric shape is positioned over the central point of the eye. The central point may be the visual axis of the eye at the surface of the cornea, or the symmetrical axis of the cornea, based on the center of the pupil.

The operator may move, rotate and resize the geometric border by interacting with the graphical user interface (GUI). The GUI allows the operator to graphically orient and position the border over the particular portion of the cornea in which the horizontal resection will be made. The software application may display zones or provide visual or audible indicators if the geometric border is positioned in an area outside of the laser operating range. For example, the display may show a general area where the geometric border may be positioned. If the geometric shape is positioned in an area not allowed for photodisruption, then the laser source will not initiate the laser beam.

The geometric border has a defined portion where the flap hinge exists. This predefined portion indicates where no photodisruption of the geometric border will occur. The hinge is indicated to the operator by a thicker and different color line than the rest of the border. The laser operator may graphically select a different side(s) or a portion of the geometric border where the hinge of the flap is to be made. In other words, the operator may change the location of the hinge and/or the length of the hinge. Also the operator may desire to remove the corneal flap altogether. To do so, the operator, would select that no hinge be made.

The boundaries of the geometric border may be defined such that the circumference of the geometric border is set at a particular distance from the center point. For example, if the shape is a circle then a parameter for the radius may be predefined at 4 mm. The software would determine the circumference, from the center point. The creation of the vertical and horizontal resection would stay within or closely about the determined circumference. If the operator wants to change the radius, then the geometric shape may be graphically resized by an input device. Alternatively, the radius distance value may be entered via an input device.

Controlling internal laser pulse parameters within scan pattern. The software may be used to alter internal pattern parameters, such as the separation distance between pulses, pulse energy, and others for the purpose of altering or varying the resection or gas/debris/fluid accumulation characteristics of the overall pattern or affecting the character of the created surfaces.

Directing laser movement The software application also allows control of the movement of the laser focus spot. A standard spot distance value is used by the software application for a particular laser source. The spot distance value is the distance the laser moves in relation to the previous spot made. Additionally, the software application uses a line separation value. For a raster pattern, this value will control the movement over to the next line where the laser will focus. For a concentric pattern a line separation value is used to determine the placement of the next concentric ring in relation to the previous concentric ring.

Selecting type of pattern cut. The software application provides the laser operator a selection for type of pattern cut. The software utilizes the selected type of pattern cut to instruct the movement of the laser beam. In one embodiment, these patterns are spiral, concentric and raster. However, other patterns may be programmed, including, but not limited to, variable reservoirs for peripheral movement or accumulation of gas or debris and control of tissue resectional separation as well as characteristics of created surfaces. Alternatively, the application may have the pattern type preset, or the pattern selection type limited. The spiral pattern generally will cause the laser to photodisrupt the corneal tissue in a spiral pattern beginning from a center point. Preferably, however, the spiral pattern begins at a starting point about the predetermined circumference to about a central point. The concentric pattern will cause the laser to photodisrupt the corneal tissue in a concentric ring pattern beginning with a central point and then photodisrupting in concentric rings around the central point. Preferably, however, the concentric ring pattern begins at a starting point about the predetermined circumference to about a central point.

The standard spot and/or line separations can be varied within a particular pattern to control or influence the character of tissue resection/separation and/or accumulation or movement of gas or debris, as well as the character of created surfaces.

Selecting additional patterns. Additionally, the software program may be configured to allow additional options for the horizontal resection. These options include: repeating the photodisruption selected pattern using the same orientation, rotating the orientation of the selected pattern and repeating, after performing a first pattern for horizontal resection, using a second pattern, or interstitial pattern. A repeated pattern may use the same or different laser parameters, such as spot separation, energy per pulse, and depth.

Selecting Reservoir and Connecting Parameters. The software application provides the laser operator a selection to create a reservoir or a connection to an existing reservoir. For example, below are some parameters that may be used for reservoir or connection creation. The primary pattern parameters are controllable to optimize use of a particular reservoir geometry and internal structure by changing spot separation, increasing or decreasing spot separation, or changing geometry (size or position) of the main pattern. This is useful when there are limitations as to placement of the reservoir.

For example, with the creation of a horizontal resection, a primary pattern of the raster type is selected, a spot separation value is set to 12, the line separation value is set to 10, the pulse energy J value is set to 5, and the depth is set to 130 µm, and the diameter is set to 8.2 mm. In the creation of a reservoir, an arc scan is selected, with a 120° reservoir angle, a radial spot separation value of 9, a tangential spot separation value of 7, pulse energy starts at 8 J and ramps down to 5 J, reservoir start depth is 160 µm, and end depth is 13.0 µm, the "width" of the reservoir is 300–400 µm.

TABLE 1

| Parameter Description | Example Values for Primary Pattern | Example Values for Secondary or Reservoir Pattern |
| --- | --- | --- |
| Laser Pulse Energy | 1–10 µJ with ability to vary energy over the pattern | 1–10 µJ with ability to vary energy over the pattern |
| Laser Pulse Separation | 2–20 microns | |
| Shape | Circular, oval | Ring, Arc, variable |

TABLE 1-continued

| Parameter Description | Example Values for Primary Pattern | Example Values for Secondary or Reservoir Pattern |
| --- | --- | --- |
| Size | 2–10 mm diameter | Variable |
| Depth | Variable | Variable |
| Start Location | Variable | Variable |

Example of Raster Pattern with a Circular Geometric Border. The following is an example of a flap created where a raster pattern has been selected to be made within a circular geometric border. A central point on the cornea is determined. This central point is given an X value of zero and a Y value of zero. To make a raster cut for a horizontal resection of stromal tissue, the focused laser begins at the maximum radius of the circular border at the most positive Y-axis location. The laser source sends a laser pulse(s) to photodisrupt corneal tissue at the current X/Y coordinate at a Z-axis depth value (the depth of the focused laser beam).

An applanation lens, an example of which is described in co-pending application U.S. Ser. No. 09/772,539, may be used to flatten the surface of the cornea to decrease or prevent spherical aberrations and coma. Thus, the Z-axis depth value (the distance from the corneal surface) for the horizontal resection may remain constant throughout the horizontal resection. Using an applanation lens and keeping the Z-axis depth value constant will result in resection of corneal tissue of generally uniform thickness. When utilizing an applanation lens device, the Z-axis depth value is typically set at 160 µm below the proximal surface of the lens contacting the cornea.

Without the use of an applanation lens or similar device, the cornea will be generally spherical. Instead of a constant depth value to create the resection to achieve a generally uniform thickness of resected corneal tissue, the Z-axis depth value will have to be controlled by the software. The eye should be fixed in a static position. A device to read the symmetry and dimensions of the eye, may be used to determine appropriate X-axis depth values. The Z-axis depth value will be varied through the resection to achieve a resection of corneal tissue of generally uniform thickness.

For the raster pattern, the laser beam photodisrupts tissue in a linear path from the highest point on the X-axis to the lowest point on the X-axis. The laser focal point is moved based on the spot separation value. The spot separation is preferably set such that the laser beam focus provides overlapping areas of photodisruption.

The focal point for photodisruption is then incrementally moved to a lower X-axis location based on the line separation value. This time the laser is positioned at the lowest point on the X-axis within the geometric border for the new Y-axis location. The laser continues through the X/Y-axis moving up the X-axis, then moving to a new Y-axis location, then moving down the X-axis. Once the line reaches the lowest X-axis value of the geometric border, then the photodisruption stops.

If a peripheral reservoir is desired, a series of pulses may be delivered before or after the raster pattern (or any other pattern) is delivered in any peripheral shape or orientation and with any specific internal parameters (spot, line separation, energy) to control gas/debris accumulation and movement as well as tissue resection/separation and surface characteristics.

For a vertical resection (side cut), the laser beam is focused within or near the circumference of the geometric border. Typically, the laser beam is focused 50 μm from the circumference. The Z-axis (or depth) of the laser focus is set at a position to focus the laser beam slightly below (typically 20 μm) the plane of the horizontal resection. The computer directs the laser beam in a path that follows the circumference of the geometric border. The speed with which the laser focus traverses the circle depends on the desired spot separation between focused pulses of light. Typically, for a circular border, the laser traverses the circumference in a counter-clockwise fashion when viewed from the user's perspective. The laser source issues a sequence of pulses into the circumference that inscribes the horizontal resection. When the circle is complete, the Z-axis of the laser focus is repositioned to a depth slightly above the initial Z-axis depth value. The laser then traverses the circumference following the same path as before and photodisrupts another layer of corneal tissue. This process is repeated until the surface of the cornea has been photodisrupted. Preferably, if using an applanation contact lens to flatten the cornea, the process continues to a few microns into the applanation contact lens. Utilizing concentric circles for the side cut creates a peripheral edge that is generally perpendicular to the X-Y axis.

Alternatively, the side cut may be made with incrementally increasing or decreasing circumferences of the geometric border. For example, given a circular geometric border, a first circular photodisrupted cut may be made at the anterior interior surface of the horizontal resection. Next, a second circular photodisrupted cut may be ma de with an increased radius at a shallower depth. Ever-increasing radii cuts at incrementally shallower depths are made until the side cut is created through the surface of the cornea. This type of cut would create a sloping peripheral edge with an angle greater than 90 degrees. In other words, the outermost circular cut at the surface of the cornea would be greater in its radius than would be the initial cut made within the corneal tissue.

Another way to make the cut is by incrementally decreasing the geometric border. In this case, a first concentric circular cut is made. The next cut would be shorter in radius than the first cut. Ever decreasing radii cuts are made, which creates a sloping peripheral edge with an angle less than 90 degrees.

Also, with the creation of vertically displaced circles of photodisrupted tissue, the radius of each successive circle may be incrementally increased by a fixed amount until the maximum radius of the vertical resection is reached.

The hinge is that part of the circumference of the geometric border where no cutting is performed. Preferably the reservoir is created near the location of the hinge. The laser beam is directed along the circumference of the geometric border. However, a continuous portion of the border is designated for the flap. No photodisruption occurs along the border designated a flap. For example, with a circular geometric border, the hinge is an arc defined by its position and angle. When the laser focus reaches a predetermined position along its circular path, the laser beams movement stops and reverses the path of the laser beam with the next circle above the previous circle. This is done for each circle comprising the vertical resection. In this manner, a portion of the vertical resection is masked, thereby creating a flap hinge. In the preferred embodiment, the reservoir angle and the hinge angle are substantially the same.

While the particular System and Method for Improved Material Processing Using a Laser Beam as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A computer-implemented method for directing a laser beam to create a resected area of corneal tissue, said method comprising:
   receiving a selection for a geometric border;
   orienting the geometric border about a display of a cornea, the geometric border having a predetermined circumference;
   receiving a selection for a type of pattern cut;
   directing the laser beam to perform photodisruption of corneal tissue to create a reservoir; and
   directing the laser beam to perform photodisruption of corneal tissue using the selected pattern cut for the selected geometric border, wherein the pattern cut forms an anterior internal surface and a posterior internal surface of the corneal tissue.

2. The computer-implemented method of claim 1, further comprising determining a central point of the cornea for positioning the circumference of the geometric border about the cornea.

3. The computer-implemented method of claim 1, wherein the cornea has an outer surface and the photodisruption is performed at a selected depth below the corneal surface.

4. The computer-implemented method of claim 1, wherein the type of pattern cut is spiral.

5. The computer-implemented method of claim 1, wherein the type of pattern cut is concentric.

6. The computer-implemented method of claim 1, wherein the type of pattern cut is rasterized.

7. The computer-implemented method of claim 1, wherein the directing a laser beam to perform photodisruption of corneal tissue forms a horizontal resection.

8. The computer-implemented method of claim 7, further comprising the step of directing the a laser beam to perform photodisruption of corneal tissue to create a vertical resection about the horizontal resection.

9. The computer-implemented method of claim 1, wherein the reservoir is peripheral to the anterior internal surface and the posterior internal surface.

10. The computer-implemented method of claim 1, wherein the reservoir is directly connected to a corneal-scleral junction of the eye.

11. The computer-implemented method of claim 1, wherein the photodisruption of corneal tissue using the selected pattern cut begins near the vicinity of the predetermined circumference.

12. The computer-implemented method of claim 1, wherein the reservoir is connected to a corneal-scleral junction of the eye via existing channels.

13. The computer-implemented method of claim 1, wherein the reservoir is connected to a corneal-scleral junction of the eye via potential corneal channels.

14. The computer-implemented method of claim 1, wherein the reservoir is created at a shallower depth relative to the an anterior internal surface and a posterior internal surface.

15. The computer-implemented method of claim 1, wherein the reservoir is created at a deeper depth relative to the an anterior internal surface and a posterior internal surface.

16. The computer-implemented method of claim 1, wherein the reservoir is created in a central location of the posterior internal surface.

17. The computer-implemented method of claim 1, wherein the reservoir is created with variable laser pulse energies and/or separations to control gas/liquid and debris accumulation.

18. The computer-implemented method of claim 1, wherein the reservoir is created by photodisruption with variable shape dimensions to control gas/liquid and debris accumulation.

19. The computer-implemented method of claim 1, further comprising the step of creating one or more additional reservoirs in the corneal tissue adjacent to the geometric border.

20. The computer-implemented method of claim 1, further comprising the step of creating passageways by photodisrupting corneal tissue from the reservoir to the geometric border.

21. The computer-implemented method of claim 1, further comprising repeating the step of directing the laser beam to perform photodisruption of corneal tissue using the selected pattern cut.

22. The computer-implemented method of claim 21, wherein the repeated directing step utilizes different laser parameters than the first directing step.

23. The computer-implemented method of claim 1, further comprising rotating the selected pattern cut and directing the laser beam to perform photodisruption of the corneal tissue using the rotated pattern cut.

24. The computer-implemented method of claim 1, further comprising selecting a second pattern cut and directing the laser beam to perform photodisruption of the corneal tissue using the second pattern cut.

* * * * *

UNITED STATES PATENT AND TRADEMARK OFFICE
CERTIFICATE OF CORRECTION

| | |
|---|---|
| PATENT NO. | : 7,189,224 B2 |
| APPLICATION NO. | : 11/083793 |
| DATED | : March 13, 2007 |
| INVENTOR(S) | : Kurtz et al. |

Page 1 of 1

It is certified that error appears in the above-identified patent and that said Letters Patent is hereby corrected as shown below:

In claim 8 (Column 16, line 41), delete "the a" and insert -- the -- therefor.

In claim 14 (Column 16, line 62), delete "the an" and insert -- the -- therefor.

In claim 14 (Column 16, line 62), delete "a posterior" and insert -- the posterior -- therefor.

In claim 15 (Column 16, line 66), delete "the an" and insert -- the -- therefor.

In claim 15 (Column 16, line 66), delete "a posterior" and insert -- the posterior -- therefor.

Signed and Sealed this

Twenty-second Day of May, 2007

JON W. DUDAS
*Director of the United States Patent and Trademark Office*